United States Patent [19]
Zerrweck

[11] 3,979,474
[45] Sept. 7, 1976

[54] PROCESS FOR SEPARATING ISOBUTYLENE FROM $C_4$ HYDROCARBON MIXTURES

[75] Inventor: Willy Zerrweck, Marl, Germany

[73] Assignee: Chemische Werke Huls Aktiengesellschaft, Marl, Germany

[22] Filed: Dec. 13, 1974

[21] Appl. No.: 532,674

[30] Foreign Application Priority Data
Dec. 14, 1973  Germany............................ 2362115

[52] U.S. Cl........................... 260/677 S; 260/677 A
[51] Int. Cl.².......................................... C07C 11/08
[58] Field of Search....................... 260/677 S, 677 A

[56] References Cited
UNITED STATES PATENTS

| | | |
|---|---|---|
| 2,424,186 | 7/1947 | Packie et al..................... 260/677 S |
| 2,961,472 | 11/1960 | Welch et al..................... 260/677 S |
| 3,005,856 | 10/1961 | Gislon et al. .................... 260/677 S |

Primary Examiner—Herbert Levine
Attorney, Agent, or Firm—Gilbert L. Wells

[57] ABSTRACT

An improvement in the process for separating isobutylene from a mixture of $C_4$ hydrocarbon by extracting with sulfuric acid, characterized in that the $C_4$ hydrocarbon mixture is extracted at a temperature between about 30° and 45°C by means of about 40 – 55 percent by weight sulfuric acid in a first stage, whereupon the extract thus obtained is converted into isobutylene and into sulfuric acid, the residual mixture of $C_4$ hydrocarbons after separating the entrained tertiary butyl alcohol is extracted in a second stage at a temperature between about 10° and 25°C by means of about 60 – 70 percent by weight sulfuric acid, the extract thus obtained being separated into sulfuric acid and into hydrocarbons (dimers and trimers).

9 Claims, 1 Drawing Figure

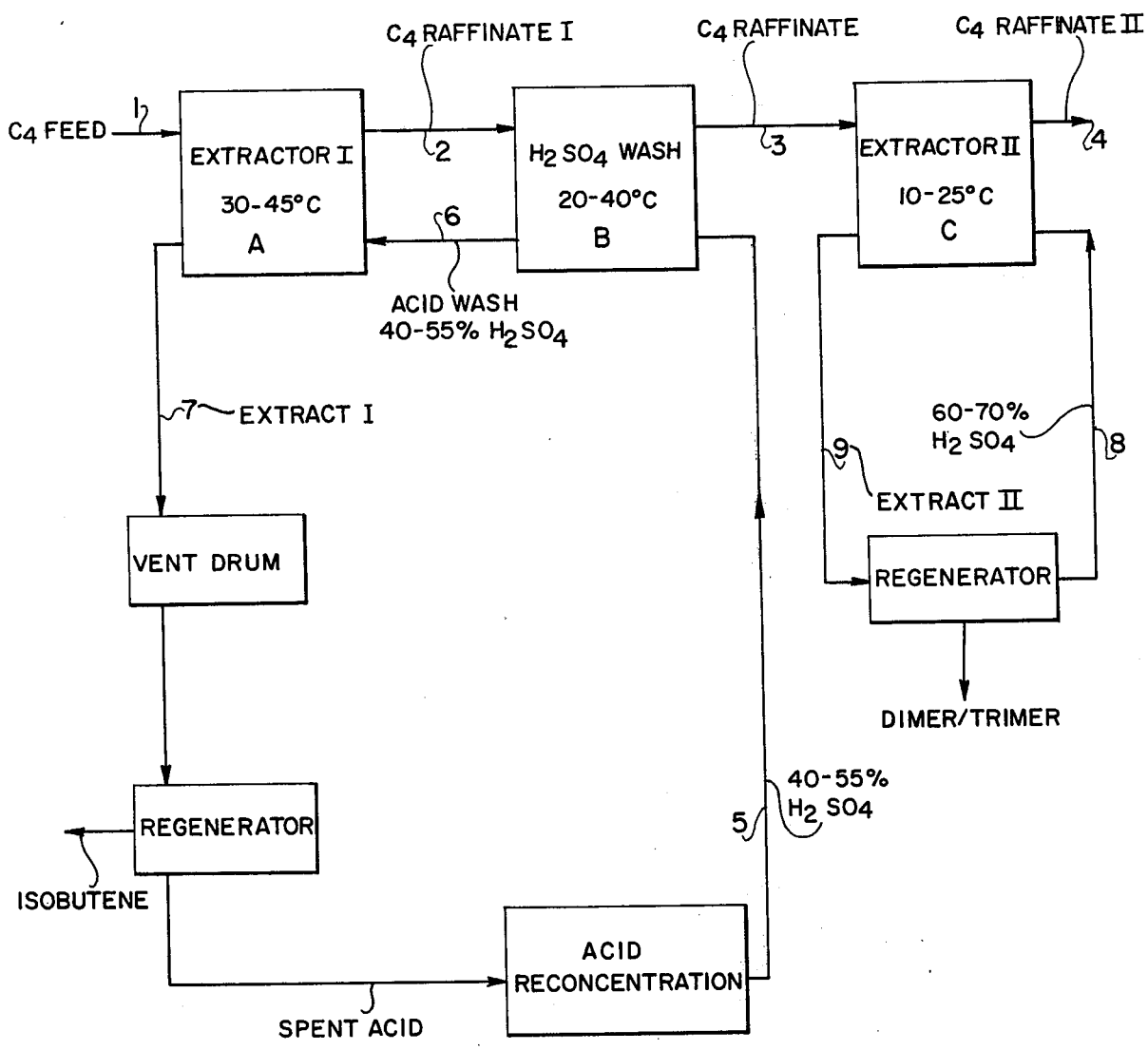

PROCESS FOR SEPARATING ISOBUTYLENE FROM C$_4$ HYDROCARBON MIXTURES

BACKGROUND OF THE INVENTION

The present invention is concerned with a process for separating isobutylene from mixtures of C$_4$ hydrocarbons by sulfuric acid extraction.

The state of the art of isobutylene refining and purification may be ascertained by reference to the Kirk-Othmer "Encyclopedia of Chemical Technology", Vol. 3 (1964), pages 830–865, under the section "Butylenes", particularly pages 836–839, and FIG. 1 on page 837, and U.S. Pat. No. 2,961,472, the disclosures of which are incorporated herein.

It is known that tertiary olefins will react more readily with sulfuric acid than primary or secondary olefins of the same C number. It is further known that this differential reactive behavior of tertiary olefins with respect to sulfuric acid is used on an industrial scale, mostly for selectively separating isobutylene from C$_4$ hydrocarbons containing isobutylene and butenes.

Mixtures of C$_4$ hydrocarbons containing olefin- and paraffin C$_4$ hydrocarbons are obtained industrially from the thermal and catalytic cracking of petroleum products and from the ethylene production by pyrolysis of light benzene or petroleum fractions of higher boiling points.

According to Kirk-Othmer ibid, Vol. 3 (1964), p. 834, typical compositions of recovered C$_4$ fractions have:

| Component of C$_4$ Fraction | Mole % |
|---|---|
| isobutane | 26.0–38.5 |
| n-butane | 6.5–9.5 |
| isobutylene | 13–19 |
| 1-butene | 9–12 |
| 2-butene | 27–37 |

Several processes for selective separation of isobutylene from mixtures of C$_4$ hydrocarbons containing isobutylene and butenes, and based on the reaction of isobutylene with sulfuric acid, are known.

The oldest sulfuric acid process is the so-called Cold Acid Polymerization Process. In the latter, isobutylene is separated by extracting with 60 – 70 percent sulfuric acid by weight. The extracted isobutylene is removed from the extraction solution as a mixture of dimers and trimers. The 60 – 70 percent by weight recovered sulfuric acid is again used for extraction of isobutylene. Isobutylene may be prepared from the mixture of dimers and trimers by depolymerization (Oil Gas 36,26, 133–42, 1937).

Later the so-called Esso Process was developed. In the latter, isobutylene is separated by means of 60 – 70 percent by weight sulfuric acid in a two-stage extraction process at two different temperatures. Then the mixture of C$_4$ hydrocarbons in the liquid phase is made to react in countercurrent flow with the acid. Prior to further processing, the extract so obtained is diluted to 45 percent by weight. When the diluted extract is recovered, isobutylene is obtained in a purity of 96 – 99 percent by weight and sulfuric acid as 45 percent by weight. The sulfuric acid so obtained must be concentrated to 60 –70 percent by weight prior to renewed use in extracting (Petroleum Refiner, 33,5, 156–9, 1954; also German Pat. No. 829,295). Processes improving the recovery of the extracted isobutylene similar to the Esso process itself yield only unsatisfactory amounts of and purities of isobutylene as disclosed in U.S. Pat. No. 2,961,472.

According to U.S. Pat. No. 2,961,472, theoretically the extraction process using concentrated aqueous solutions of sulfuric acid merely consists in the commercial exploitation of the following well known chemical reaction:

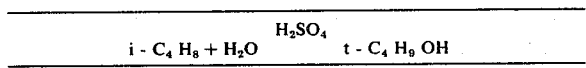

$$i\text{-}C_4H_8 + H_2O \xrightarrow{H_2SO_4} t\text{-}C_4H_9OH$$

The tertiary butyl alcohol is soluble in sulfuric acid, and so the sulfuric acid phase, containing the dissolved tertiary butyl alcohol, is separated from the hydrocarbon phase. Since the original reaction is reversible and isobutylene is the desired end product, the isobutylene may be recovered by the application of heat to the sulfuric acid solution of the tertiary butyl alcohol.

The process of U.S. Pat. No. 2,961,472 is an improvement over the process of selectively extracting isobutylene from a mixture of C$_4$ hydrocarbons comprising olefins and paraffins in addition to the isobutylene by reacting the C$_4$ hydrocarbon mixture with an aqueous solution of sulfuric acid to convert the isobutylene to tertiary butyl alcohol soluble in the aqueous sulfuric acid. The sulfuric acid solution is separated from the C$_4$ hydrocarbon mixture and the tertiary butyl alcohol in the sulfuric acid solution is regenerated to isobutylene. The extraction sulfuric acid from the regeneration is reconcentrated by vacuum distillation and has a maximum of 2.0 percent by weight of non-aqueous impurities therein. The sulfuric acid solution containing tertiary butyl alcohol and physically entrained and dissolved hydrocarbon impurities is passed to a venting zone maintained at a temperature of 135°–150°F prior to the regeneration of the isobutylene.

With regard to a further process, the so-called CFR process, 50 percent by weight sulfuric acid is used. Isobutylene is separated in a multi-stage extraction process in a manner similar to and under similar conditions as in the Esso process. There is no dilution of the extract obtained prior to recovery. The latter yields isobutylene of a purity exceeding 99 percent by weight and 50 percent by weight sulfuric acid, this 50 percent sulfuric acid being used again for extraction (Erdoel und Kohle, 16, 100–4, 1963).

Lastly, BASF has developed a process wherein 45 percent by weight sulfuric acid is used for obtaining isobutylene; a mixture of C$_4$ hydrocarbons in the gaseous state is made to react with sulfuric acid in bubble columns. Tertiary butanol is isolated at temperatures up to 50°C and at lowered pressures from the extraction solution obtained. The recovered acid is then used again for extraction. The isolated tertiary butanol is converted into isobutylene of a purity exceeding 99.9 percent by weight by means of a dehydration catalyst (Erdoel und Kohle 22, 605–8, 1969).

The previously known processes yield isobutylene and refined C$_4$ hydrocarbons of varying qualities. The purer the isobutylene obtained from these processes, the higher the isobutylene content in the refined C$_4$ hydrocarbons. The latter factor is a drawback if highly pure isobutylene and refined C$_4$ hydrocarbons practically free from isobutylene are simultaneously required. Refined C₄ hydrocarbons containing more than 0.5 percent by weight of isobutylene are virtually unusable for certain applications such as the preparation of secondary butanol, or of methylethyl ketone and 1-butene with a purity exceeding 99 percent by weight.

SUMMARY OF THE INVENTION

Having in mind the limitations of the prior art, it is an object of the present invention to create a process allowing practically complete separation of isobutylene from mixtures of C₄ hydrocarbons by sulfuric acid extraction.

This object of the present invention is achieved in that the mixture of C₄ hydrocarbons is subjected to extraction in a first stage at a temperature of about 30° – 45°C by means of about 40 – 55 percent by weight sulfuric acid, whereupon the extract obtained is separated into isobutylene and sulfuric acid, the remaining mixture of C₄ hydrocarbons after separating the entrained tertiary butyl alcohol being subjected to extraction in a second stage at a temperature between 10° and 25°C with 60 – 70 percent by weight sulfuric acid, the extract from this second stage being separated into sulfuric acid and hydrocarbons (dimers and trimers).

BRIEF DESCRIPTION OF THE DRAWING

Further details and characteristics of the process of the present invention are made clear in the following description with reference to the attached flow diagram.

Input mixture 1 which is a mixture of C₄ hydrocarbons containing predominantly isobutylene and butenes, is reacted with the washing acid 6 from wash (B) in the extraction facility (A) at a temperature between about 30° and 45°C. The C₄ hydrocarbon feed mixture may be extracted by means of the acid in the liquid or gaseous state. Extraction facility (A) may consist of one or several reaction steps, as disclosed in U.S. Pat. No. 2,961,472. Following separation of the extract mixture into extract I 7 and into raffinate C₄ hydrocarbons I 2, the tertiary butyl alcohol formed in (A) and carried along to (B) is washed out of (B) at a temperature between about 20° and 40°C with about 40 – 55 percent by weight sulfuric acid 5 in wash (B). The raffinate C₄ hydrocarbons 3 rid of tertiary butyl alcohol reach extraction facility (C), where the residual isobutylene still in the raffinate C₄ hydrocarbons I is extracted to less than a content of 0.2 percent by weight by reaction with about 60 – 70 percent by weight sulfuric acid 8 at a temperature between about 10° and 25°C. The reaction product from reaction facility (C) is separated into extract II 9 and into raffinate C₄ hydrocarbons II 4. Extract I yields isobutylene exceeding a purity of 99 percent by weight and extract II yields a mixture of dimers and trimers. The process of the present invention when contrasted with the state of the art allows separating isobutylene from a mixture of C₄ hydrocarbons in surprisingly simple manner to such an extent that only less than 0.2 percent by weight of isobutylene remains in the hydrocarbons. Furthermore, highly pure isobutylene or dimers or trimers may be obtained simultaneously.

DESCRIPTION OF THE PREFERRED EMBODIMENTS

In the process of the present invention, a mixture of C₄ hydrocarbons may be used, which contains more than about 10 percent by weight of isobutylene.

The C₄ fractions recovered by the present invention have the following general compositions:

| Component of C₄ Fraction | Weight % |
|---|---|
| isobutane | 1–40 |
| n-butane | 6–10 |
| isobutylene | 10–50 |
| 1-butene | 9–30 |
| 2-butene | 15–40 |

The process of the present invention is carried out in two stages. Several steps may be used in the first one and generally a single step is required in the second.

The mixture of C₄ hydrocarbons used is extracted in conformity with the present invention with about 40 – 55 percent by weight sulfuric acid in the first stage, preferably with about 48 – 55 percent by weight of sulfuric acid. If several steps are used in the first stage, the mixture of hydrocarbons generally is made to pass in counterflow through the sulfuric acid as disclosed in U.S. Pat. No. 2,961,472.

For acid concentrations higher than indicated above, the selectivity of the isobutylene separation drops and the purity of the isobutylene obtained decreases. For acid concentrations that are too low, on the other hand, the rate of reaction decreases and the isobutylene content in the hydrocarbon rafinate increases.

According to the concept of the invention, a temperature of about 30° to 45°C is used. For a temperature in excess of 45°C polymerization is initiated. For a temperature under 30°C, the reactivity falls off and the concentration of isobutylene in the C₄ hydrocarbon raffinate increases.

The extract thus obtained is separated from the residual hydrocarbon raffinates in a separation vessel when the input product in liquid phase reaches reaction. The extract is separated as the sump product of the reaction column when the input mixture is applied in gaseous form. The extract proper is recovered in conventional manner to isobutylene. The isobutylene is obtained in purities exceeding 99 percent by weight. The separated sulfuric acid is again used for extraction, as disclosed in U.S. Pat. No. 2,961,472.

The further and practically complete separation of isobutylene thereupon takes place in a second stage by extracting with about 60 – 70 percent by weight sulfuric acid at a temperature from about 10° to 25 °C. Similar to the first stage, the mixture of hydrocarbons to be extracted generally is made to react with sulfuric acid in a reaction step. If the sulfuric acid concentrations are too low and/or higher temperatures are applied there will be insufficient extraction of isobutylene. For excessive acid concentrations, butenes also are extracted more intensively. It is also a drawback to use temperatures that are too low, because of the economics of the situation and the receding rates of reaction. Isobutylene contained in the extract from the second stage partially as tertiary butyl alcohol is converted into dimers and trimers of isobutylene. Extract conversion into sulfuric acid and hydrocarbons takes place at temperatures ranging from about 70° to 120°C and at pressures ranging from about 4 to 15 atmospheres.

The Table below shows the results from this procedure.

| | COMPOSITIONS % By Weight | | | |
|---|---|---|---|---|
| | Input C$_4$ hydrocarbons (1) | Raffinate C$_4$ hydrocarbons I (2) | Raffinate C$_4$ hydrocarbons II (4) | Isobutylene Products |
| i-C$_4$H$_{10}$ | 1.69 | 3.46 | 3.42 | — |
| n-C$_4$H$_{10}$ | 8.93 | 16.22 | 18.32 | — |
| 1-C$_4$H$_8$ 1-butene | 24.93 | 46.06 | 46.63 | 0.06 |
| i-C$_4$H$_8$ isobutylene | 48.73 | 5.80 | 0.14 | 99.60 |
| tr.-2-C$_4$H$_8$ trans-2 butene | 8.92 | 16.80 | 18.99 | 0.17 |
| cis-2-C$_4$H$_8$ cis-2-butene | 6.67 | 11.40 | 12.17 | 0.16 |
| 1.3-C$_4$H$_6$ | 0.10 | 0.19 | 0.20 | — |
| C$_5$ hydrocarbons | 0.03 | 0.07 | 0.09 | — |

The residual C$_4$ hydrocarbon raffinate from the second stage is separated from the extract in a manner similar to the first step in a separation vessel and the raffinate contains less than 0.2 percent by weight of isobutylene.

The mixture of hydrocarbons used in the process of the present invention may be made to react with sulfuric acid in either the gaseous state or under pressure in the liquid one. As a rule, the input mixture is extracted in the liquid phase in industry because of technical and economic considerations, as disclosed in U.S. Pat. No. 2,961,472.

Because the tertiary butyl alcohol occurring during extraction in the first stage and carried along with the C$_4$ hydrocarbon raffinate of the first stage reach the second stage and interfere with the procedure of the latter, the tertiary butyl alcohol is separated from the C$_4$ hydrocarbon raffinate of the first stage. This may be done by distillation or by washing with sulfuric acid. The simplest of the various possibilities consists in washing out the tertiary butyl alcohol with the 40 – 55 percent by weight sulfuric acid required for the first stage extraction while making use of the washing acid so obtained for extracting the isobutylene in the first stage. If the tertiary butyl alcohol is not separated, there will be needed a compensation of the concentration of the sulfuric acid in both stages after some time.

The following example will further illustrate the invention.

EXAMPLE 4,750 kg of a mixture of C$_4$ hydrocarbons predominantly containing isobutylene and butenes are reacted at a pressure of 8 atmospheres and at 35°C with 7,320 kg of washing acid obtained when the tertiary butyl alcohol is washed out of the C$_4$ hydrocarbon raffinate I at 7.5 atmospheres and 30°C with 7,200 kg of 53 percent by weight sulfuric acid. The reaction mixture is separated in a separation vessel into extract I and into C$_4$ hydrocarbon raffinate. 2,055 kg of isobutylene are obtained from extract I following separation of the physically dissolved C$_4$ hydrocarbons and following heating.

The washed C$_4$ hydrocarbon raffinate 3 thereupon is reacted with 5,850 kg of 63 percent by weight sulfuric acid at 20°C and at a pressure of 7 atmospheres. Extract II and C$_4$ hydrocarbon raffinate II are separated from the reaction mixture thus obtained in a separation vessel. 150 kg of dimers and trimers are obtained from extract II.

I claim:
1. In the process of selectively extracting isobutylene from a hydrocarbon mixture of C$_4$ hydrocarbons comprising olefins and paraffins in addition to said isobutylene by reacting said hydrocarbon mixture with a first aqueous solution of sulfuric acid to convert said isobutylene to tertiary butyl alcohol soluble in said first aqueous solution, separating said first aqueous solution from a raffinate comprising the remaining hydrocarbon mixture and entrained tertiary butyl alcohol and regenerating said tertiary butyl alcohol in said first aqueous solution to isobutylene, the improvement comprising:
   a. extracting said hydrocarbon mixture in a first stage at a temperature between about 30° and 45°C with said first aqueous solution having about 40 – 55 percent by weight sulfuric acid and separating a first raffinate and a first extract comprising tertiary butyl alcohol; and
   b. extracting said first raffinate after separating the entrained tertiary butyl alcohol by washing with aqueous sulfuric acid at a temperature between 20° and 40°C in a second stage at a temperature between 10° and 25°C with a second aqueous solution having about 60 – 70 percent by weight sulfuric acid and separating a second raffinate comprising remaining hydrocarbon substantially free of isobutylene and a second extract which is regenerated to recover dimers and trimers of isobutylene.

2. The process of claim 1, wherein said first aqueous solution in said first stage has about 48 – 54 percent by weight sulfuric acid and said first aqueous solution in said second stage has about 62 – 66 percent by weight sulfuric acid.

3. In the process of selectively extracting isobutylene from a hydrocarbon mixture of C$_4$ hydrocarbons comprising olefins and paraffins in addition to said isobutylene by reacting said hydrocarbon mixture with a first aqueous solution of sulfuric acid to convert said isobutylene to tertiary butyl alcohol soluble in said aqueous solution, separating said first aqueous solution from a raffinate comprising the remaining hydrocarbon mixture and entrained tertiary butyl alcohol and regenerating said tertiary butyl alcohol in said first aqueous solution to isobutylene, the improvement comprising:
   a. extracting said hydrocarbon mixture in a first stage at a temperature between about 30° and 45°C with said first aqueous solution having about 40 – 55 percent by weight sulfuric acid and separating a first raffinate and a first extract comprising tertiary butyl alcohol;

b. washing said first raffinate continuously with aqueous sulfuric acid at a temperature between 20° and 40°C to remove entrained tertiary butyl alcohol in a wash extract and produce a washed first raffinate; and c. extracting said washed first raffinate in a second stage at a temperature between about 10° and 25°C with a second aqueous solution having about 60 – 70 percent by weight sulfuric acid and separating a second raffinate comprising remaining hydrocarbons substantially free of isobutylene and a second extract which is regenerated to recover dimers and trimers of isobutylene.

4. The process of claim 3, wherein said washing step (b) is carried out at a temperature between about 20° and 40°C with said first aqueous solution having about 40 – 55 percent by weight sulfuric acid and said wash extract is used as said aqueous solution of step (a).

5. The process of claim 4, wherein said first aqueous solution in said first stage has about 48 – 54 percent by weight sulfuric acid and said second aqueous solution in said second stage has about 62 – 66 percent by weight sulfuric acid.

6. The process of claim 2, wherein said second rafinate contains less than 0.2 percent by weight of isobutylene and said first extract yields isobutylene exceeding a purity of 99 percent by weight.

7. The process of claim 5, wherein said second raffinate contains less than 0.2 percent by weight of isobutylene and said first extract yields isobutylene exceeding a purity of 99 percent by weight.

8. The process of claim 2, wherein said second raffinate contains 0.14 percent by weight of isobutylene and said first extract yields isobutylene having a purity of 99.6 percent by weight.

9. The process of claim 5, wherein said second raffinate contains 0.14 percent by weight of isobutylene and said first extract yields isobutylene having a purity of 99.6 percent by weight.

* * * * *